(12) United States Patent
Ringeisen et al.

(10) Patent No.: US 8,551,514 B2
(45) Date of Patent: Oct. 8, 2013

(54) GEL SUITABLE FOR IMPLANTATION AND DELIVERY SYSTEM

(75) Inventors: Timothy A. Ringeisen, Exton, PA (US); William Christian Wattengel, West Chester, PA (US)

(73) Assignee: Kensey Nash BVF Technology LLC, Wilmington, DE (US)

( * ) Notice: Subject to any disclaimer, the term of this patent is extended or adjusted under 35 U.S.C. 154(b) by 762 days.

(21) Appl. No.: 12/316,798

(22) Filed: Dec. 15, 2008

(65) Prior Publication Data

US 2009/0175944 A1    Jul. 9, 2009

Related U.S. Application Data

(63) Continuation of application No. 10/785,665, filed on Feb. 23, 2004, now abandoned.

(51) Int. Cl.
*A61F 2/02*    (2006.01)

(52) U.S. Cl.
USPC ......................................................... 424/425

(58) Field of Classification Search
None
See application file for complete search history.

(56) References Cited

U.S. PATENT DOCUMENTS

| | | |
|---|---|---|
| 4,689,399 A | 8/1987 | Chu |
| 4,743,229 A | 5/1988 | Chu |
| 4,772,419 A | 9/1988 | Malson et al. |
| 5,409,703 A | 4/1995 | McAnalley et al. |
| 5,531,791 A | 7/1996 | Wolfinbarger |
| 5,645,583 A | 7/1997 | Villain et al. |
| 6,066,325 A | 5/2000 | Wallace et al. |
| 6,432,437 B1 | 8/2002 | Hubbard |
| 6,488,952 B1 | 12/2002 | Kennedy et al. |
| 6,599,515 B1 | 7/2003 | Delmotte |
| 7,135,027 B2 | 11/2006 | Delmotte |
| 2002/0032488 A1 | 3/2002 | Brekke et al. |
| 2004/0009205 A1 | 1/2004 | Sawhney |
| 2004/0010224 A1 | 1/2004 | Bodmeier |

FOREIGN PATENT DOCUMENTS

| | | |
|---|---|---|
| WO | WO-98/35653 | 8/1998 |
| WO | WO-03/039615 | 5/2003 |
| WO | WO-2004/060425 | 7/2004 |
| WO | WO-2004/112854 | 12/2004 |

*Primary Examiner* — Carlos Azpuru
(74) *Attorney, Agent, or Firm* — Jeffrey R. Ramberg

(57) ABSTRACT

The invention concerns a dried form of a porous polymer gel material which may be rehydrated and placed under pressure or compression to induce salvation, thereby forming a high concentration gel, in the form of an injectable viscous putty or dough, which may be implantated in the body.

13 Claims, 6 Drawing Sheets

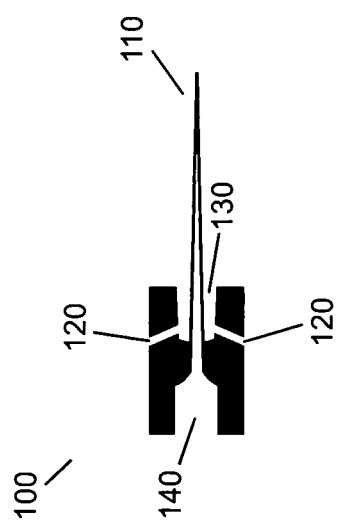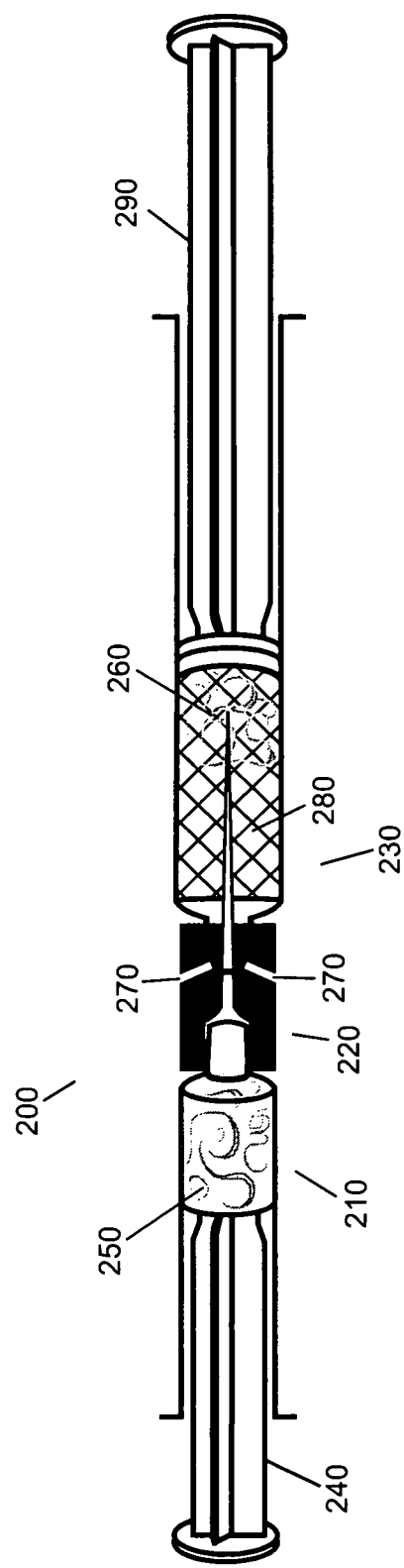

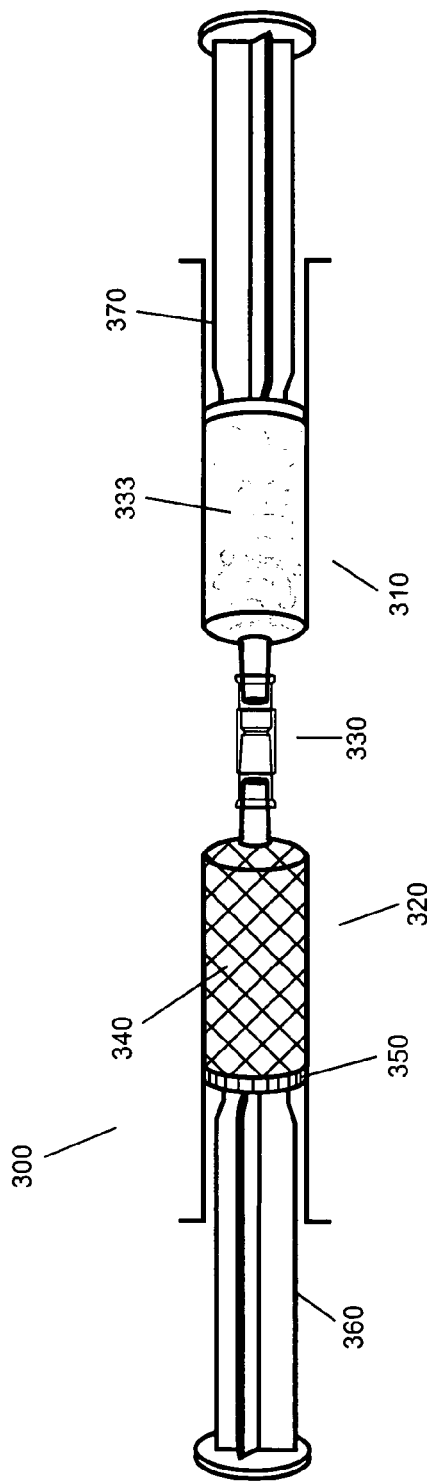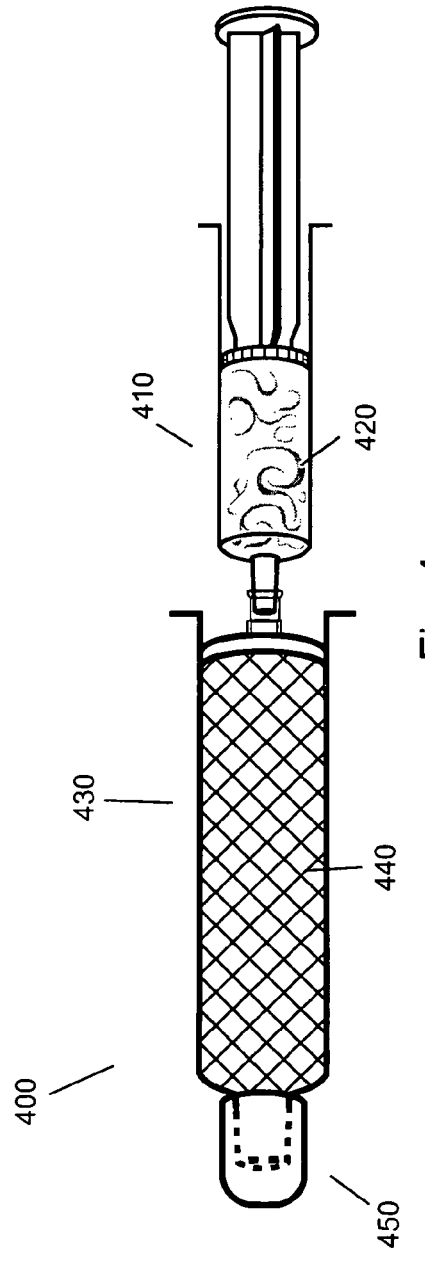
Fig. 3
Fig. 4

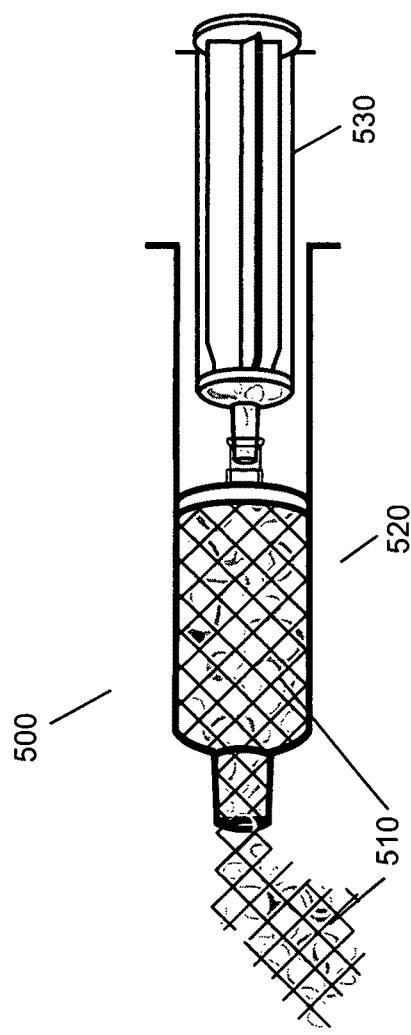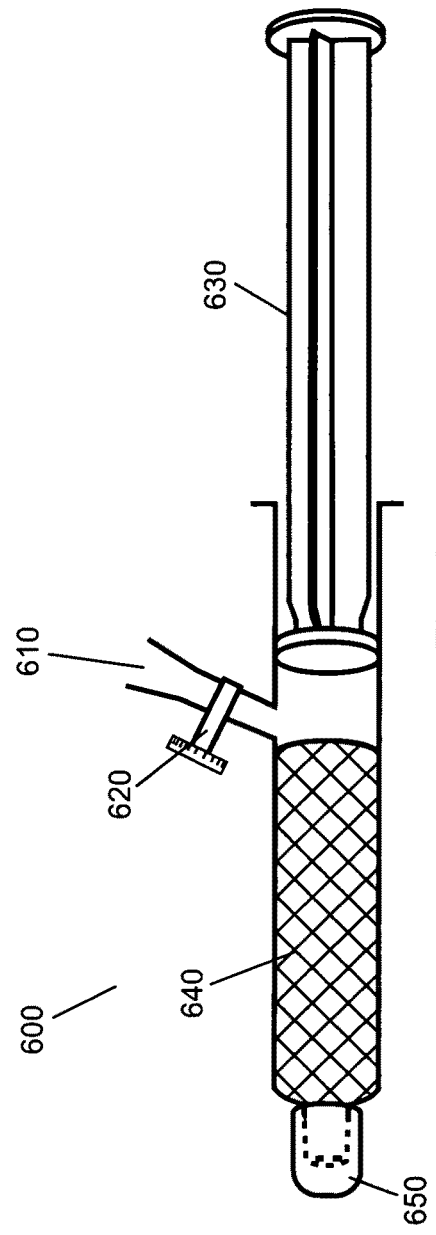

GEL SUITABLE FOR IMPLANTATION AND DELIVERY SYSTEM

CROSS REFERENCE TO RELATED APPLICATION

The present patent document is a Continuation of U.S. patent application Ser. No. 10/785,665, filed on Feb. 23, 2004, now abandoned in the names of Timothy A. Ringeisen et al., and entitled "Gel suitable for implantation and delivery system". The contents of this related patent application is hereby fully incorporated by reference.

BACKGROUND OF THE INVENTION

1. Field of the Invention

This application relates generally to medical implant devices and methods of use, specifically relating to the preparation of an implantable device, the sterilization and storage of the device, and the use and delivery of the device. The material of the present invention may serve as an implantable material in order to aid tissue healing, serve as a void filler, prevent adhesions, and/or serve as a drug delivery vessel, among other beneficial uses.

2. Discussion of Related Art

Hydrogels may be formed from a variety of polymeric materials and are useful in a variety of biomedical applications, for example, wound management, soft contact lens construction, surgical applications, and drug delivery applications. To be suitable for implantation in a living being, the polymer material should be sterile to minimize opportunity for infection. An implantable polymer material may be manufactured through an aseptic manufacturing process, where care is taken to ensure sterility through the entirety of the manufacturing process, which is costly; or alternatively, sterilization may be accomplished by terminal sterilization, which is accompanied by the concomitant benefits of reduced cost and complexity. Terminal sterilization may be accomplished by methods known in the art (e.g., high energy radiation, heat, or chemical treatment).

It is commonly known that high energy sterilization (e.g., gamma irradiation, e beam radiation, etc.) results in changes to polymers (e.g., molecular weight loss, cross-linking, etc.) that may be undesirable in the final product. It is also known that these changes are more severe when the product is in a hydrated or solvated state. It is additionally known that forms of gas sterilization (e.g., plasma, ETO, etc.) usually result in few changes to the polymers, however gas sterilization techniques may only be applied to dry products. A need exists for an implantable dough, putty or gel capable of being terminally sterilized without deleterious effects.

In U.S. Pat. No. 5,409,703, McAnalley et al. describe a topical wound dressing made from a dried hydrogel of hydrophilic-hygroscopic polymer, which is capable of being sterilized. Upon topical application to the wound site, the dried hydrogel absorbs tissue fluids and changes from a solid state to a gel state wherein it adheres to the wound surface. McAnalley also describes that in applications where the traumatized area does not require exudate removal, the device may be applied as a hydrogel, by presoaking the dried gel in saline or other therapeutic liquid/suspension.

In U.S. patent application Ser. No. 10/616,055 Sawhney describes a polymer hydrogel to be introduced to a wound site as a relatively dry material in a substantially deswollen state; it may optionally contain therapeutic entities. Upon implantation and exposure to physiological fluids, the dried hydrogel absorbs fluids and undergoes a volumetric expansion, resulting in a sealing, plugging or augmentation of tissue.

In U.S. Pat. No. 5,645,583, Villain et al. disclose an injectable, non-resorbable permanent corneal implant of polyethylene oxide gel that has been crosslinked, wherein the implanted gel serves to replace or augment tissue. The crosslinked gel may be delivered through a syringe. The injectable gel material of Villain et al. serves to prevent the ingrowth or colonization of cells and vessels into the material in order to maintain optical clarity and allow removal of the implant. The Villain et al. disclosure describes the material as being subject to postoperative volume changes, depending on the electrolyte concentration of the original material, and the environment into which the implant is introduced. Villain et al. do not describe an implant that is a pre-operatively swollen rehydrated gel material, serving to encourage the ingrowth of tissue and cells into the resorbable structure.

Delmotte, in U.S. Pat. No. 6,599,515, describes the making of a fibrin sponge, created from a solution containing fibrin, wherein the fibrin undergoes partial clotting (modulated by the addition of thrombin to the solution) and is partially cross-linked, which is then dried by lyophilization. When rehydrated, the fibrin sponge material retains its structure, merely expanding in size as fluid is absorbed into the sponge. The fibrin sponge may be milled or ground into a small grain size particulate material, may be admixed with other solid particles, such as bone chips, and suspended in a viscous gel to form a glue or cement for filling a bone void. Preferably the mixture would be made as a paste or in a substantially liquid form, in order to ease application. Delmotte also describes the material of the invention being used as a bone substitute, wherein the fibrin sponge material of the invention is hydrated with a solution before use. The material described by Delmotte must be milled or ground into particles in order to allow the creation of a paste suitable for use in filling a bone void. Delmotte does not address the need for a material that does not require milling or grinding before the addition of a liquid or glue in creating a bone void filling material.

Bodmeir in US Application 2004/0010224 discloses the use of a porous lyophilized material, that when exposed to a solvent causes the dissolution of the material, and may form a viscous liquid that is able to be implanted into the body and serve as a drug depot. As the original solvent is removed from the material, the implanted viscous liquid will harden in the presence of aqueous fluids, such as a physiological environment. The implantable material described by Bodmeir undergoes a phase change, from liquid to solid once it is implanted. Bodmeir does not describe an implant that remains a putty or dough after implantation, until eventual resorption into the body.

Malson et al. in U.S. Pat. No. 4,772,419 describes a crosslinked hyaluronic acid (or salt thereof) gel material that may be formed into a shaped article by pressure-drying or freeze-drying. The crosslinked hyaluronic material may be stored dry, and implanted or placed upon a body in dry form, or alternatively after being rehydrated in a saline solution. The crosslinking present in the material causes the material to be rehydrated as a sponge, wherein the structure is maintained, rather than forming a flowable hydrogel or putty.

Kennedy et al. in U.S. Pat. No. 6,488,952 discloses a semisolid therapeutic delivery system for injection, deposition, or implantation within the body to deliver therapies to the body. The semisolid material is formed by application of heat to melt Glycerol Monooleate or other materials having similar physical/chemical properties with respect to viscosity/rigidity, then admixing a warm aqueous buffer solution to form a gel. To the gel is added the various therapies or particulate material for systemic or local delivery to the body once implanted. The viscosity may be varied by controlling water content. The gel of sufficient viscosity forms a malleable material that may be delivered and manipulated in an implant site. Kennedy et al. do not disclose a gel material that may be dried, and rehydrated for implantation without adding heat and/or heated solutions.

Hubbard in U.S. Pat. No. 6,432,437 discloses a biocompatible material for permanent soft tissue augmentation. The material is substantially non-resorbable, ceramic spheroidal particles that are implanted and serves as a scaffold to allow tissue ingrowth. The ceramic particles can be suspended for delivery in a lubricious polysaccharide gel carrier and lubricant. The composite material of ceramic particles and gel may be stored for an indefinite period without settling of the particles, provided that the ceramic particles are of a sufficiently small size, on the order of less than 125 microns. The gel material disclosed by Hubbard is sterilizable through autoclaving, although it suffers a reduction in viscosity. The gel material is unsuitable for gamma sterilization as the gel is destroyed. Hubbard does not disclose a gel material that may be readily gamma sterilized, stored dry, and then be rehydrated to form a viscous injectable putty or dough for implant.

Wolfinbarger in U.S. Pat. No. 5,531,791 describes an injectable/flowable viscous composite of demineralized bone material and a collagen carrier, for use in bone repair. The demineralized bone component may be stored separate from a dried or lyophilized collagen carrier matrix. The bone cement and the matrix may be rehydrated and mixed, immediately before implantation; alternatively, the composite materials may be stored as a wet mixture.

Wolfinbarger discloses a collagen matrix material that may be lyophilized for storage, and rehydrated by the sterile addition of saline solution and demineralized bone component to a final collagen concentration of one to two percent. The concentrations of collagen described by Wolfinbarger will solubilize simply by the addition of saline, without requiring additional techniques to achieve solubilization.

Damien et al. in WO9835653 disclose a dry osteoinductive composition made by the process of admixing collagen, acid, osteoinductive material, and water to form a gel, which is lyophilized. The resulting dried gel is described as being able to withstand dry sterilization, such as gamma radiation sterilization or chemical treatment, and avoids chemical reactions that would otherwise occur when sterilizing wet material through similar techniques. The lyophilized material described by Damien et al. may be rehydrated simply by adding water to form a gel. WO9835653 discloses a collagen gel made by solubilizing 100 mg of collagen in 7.4 mL aqueous acid solution (1.35% collagen w/v), which is then lyophilized. A 15 mg sample of the dried collagen material is then rehydrated to a similar concentration as the original gel, as 1.14 mL of water is simply added to 15 mg of dried collagen material (1.31% collagen w/v), forming the rehydrated gel.

A need exists for an implantable material that is suitable for dry sterilization techniques, eliminating the need to be aseptically processed, thereby reducing costs. Further, a need exists for a dried, sterilized material suitable for extended storage, without settling or stratification of the material or fear of degradation, unlike a wet material. The material, to be most beneficial, should be deliverable into the body as an injectable viscous putty or dough.

Chu in U.S. Pat. No. 4,743,229 discloses a syringe system for preparing inductive and conductive bone repair compositions. The device described by Chu allows the mixing of a substantially uniform collagen/mineral bone implant preparation, incorporating a pair of syringes facing each other, with a connective adapter arranged between the delivery ends. By application of force on the barrel containing the collagen solution, the fluid is forced into the barrel of the other syringe containing the particulate material. Air within the mineral particulate is displaced by the inflow of fluid, and escapes through a porous barrier at the opposite end of the particulate material syringe. Chu does not disclose or contemplate a phase transition during mixing as the collagen solution is directed into the particulate material.

A need exists for a high viscosity material suitable for injection or in-situ molding supplied in dry form, which is readily and quickly rehydratable or resolvable upon addition of fluid (e.g., blood, saline, water, acetone, etc.), which facilitates cellular ingrowth. It is the intent of this invention to overcome these and other shortcomings of the prior art.

SUMMARY OF THE INVENTION

Disclosed is an implantable gel material, which in a preferred embodiment may be formed from a pressure solubilized dried gel, by hydrating through the addition of a solvating fluid and the application of a pressurizing force. Additionally, the solvating fluid or the gel itself may contain a biologically active agent(s) and/or a filler material(s).

The resulting implant may contain, at least in part, a polymer (e.g., natural or synthetic); which may be malleable following rehydration and salvation.

The rehydration step or process, in a preferred embodiment, comprises adding less fluid than was removed during the dehydration step. Additionally the solvation step, being a pressure solubilization process, causes solubilization at a faster rate than would typically occur by capillary rehydration or stagnant solvation.

A preferred embodiment of the present invention may be produced by a process comprising the steps of providing a biomaterial having a large surface area, and a fluid; combining the biomaterial with the fluid, wherein the surface area of the biomaterial becomes coated with the fluid; and applying a pressurizing force to the combined fluid and biomaterial wherein the biomaterial collapses into a malleable gel.

In this process, the solvating fluid or the gel itself may contain a biologically active agent(s) or a filler material(s).

DESCRIPTION OF THE DRAWINGS

FIG. 1 is a view of a syringe hydration needle.

FIG. 2 is a view of a syringe hydration needle attached to a delivery syringe and receiving syringe.

FIG. 3 is a view of a delivery syringe and receiving syringe connected via an adapter.

FIG. 4 is a view of a delivery syringe connected to a back loading receiver syringe.

FIG. 5 is a view of a delivery syringe expelling gel out of a back loading receiver syringe.

FIG. 6 is a view of a receiving syringe with a fluid injection port.

DETAILED DESCRIPTION OF PREFERRED EMBODIMENTS

Figure 7:
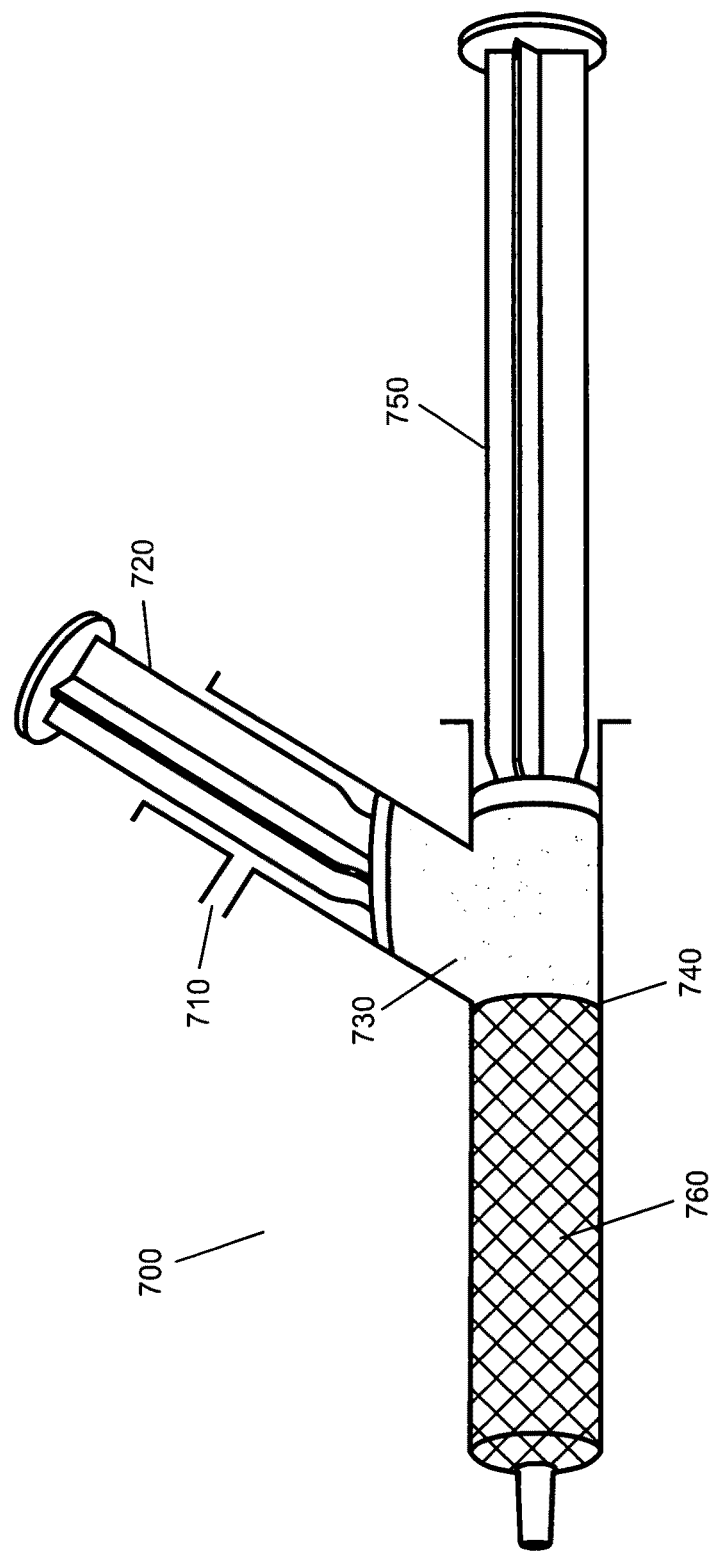
FIG. 7 is a view of a combination delivery-receiving syringe.

The prior art described does not disclose an implantable, resorbable hydrogel material formed by adding fluid to a dried porous material, and solvating under pressure. The rehydration and solvation of the material forms a viscous gel, dough or putty that encourages the ingrowth of cells and vessels for tissue repair and augmentation.

The following description describes the compositions, devices, and methods for practicing the present invention. The present invention provides a high porosity biomaterial (e.g., natural and synthetic polymers, ceramics, etc.) having a high surface area to volume ratio and interconnected pores capable of rapidly hydrating when placed in contact with a fluid, and rapidly solubilizing when placed under compression or pressure after being infiltrated with a fluid. The resultant gel is believed to occur from the formation of a high concentration solution, colloidal suspension or combination of the two. The concentration necessary to create a gel will vary and be dependant on the biomaterial and/or hydration or solvation fluids selected in practicing the present invention.

In a preferred embodiment, highly viscous polymer gels of the current invention are produced by freeze-drying low concentration solutions into a high porosity foam having a high surface area to volume ratio and interconnected pores, and rehydrating with a lesser volume of fluid under pressure than was removed during freeze-drying. The freeze-dried foam may further be shaped, cut and/or packaged in a variety of forms (e.g., disks, cubes, bars, cylinders, granules, etc.) Alternatively, one may also create intercommunicating porosity within a single construct by methods known in the art such as particulate leaching, precipitation, sintering and/or electrospinning.

In practice of the present invention, the dried porous material is exposed to fluid and undergoes hydration and pressure induced solubilization. During hydration, fluid flows into the porous construct, filling the pores and coating the internal and external surfaces of the polymer sponge. During solubilization, the fluid is forced under pressure into the mass of polymer that creates the partitions of the construct, resulting in collapse of the sponge as a solution or colloidal suspension is formed. The polymer can be selected from one or more materials capable of forming a viscous gel upon solvation. (e.g., poly lactic acids (PLA), poly lactic coglycolic acids (PLGA), collagen, hyaluronic acic (HY), alginate, chitosan, glycosaminoglycans (GAGS), etc.). Other resorbable and non-resorbable polymer materials may be suitable for practicing this invention. The appropriate polymer matrix or material to be processed in practicing the present invention may be determined by several factors including, but not limited to, the desired mechanical and material properties, the surgical application for which the material is being produced, and the desired degradation rate of the device in its final application. Examples of resorbable polymers that can be used are shown in following Table 1. These materials are only representative of the materials and combinations of materials, which can be used in the practice of the current invention.

TABLE 1

Examples of Biodegradable Polymers for Construction of the Device

Aliphatic polyesters
Alginate
Cellulose
Chitin
Chitosan
Collagen
Copolymers of glycolide
Copolymers of lactide
Elastin TABLE 1-continued Examples of Biodegradable Polymers for Construction of the Device Fibrin
Glycolide/l-lactide copolymers (PGA/PLLA)
Glycolide/trimethylene carbonate copolymers (PGA/TMC)
Glycosaminoglycans
Hydrogel
Lactide/tetramethylglycolide copolymers
Lactide/trimethylene carbonate copolymers
Lactide/$\epsilon$-caprolactone copolymers
Lactide/$\sigma$-valerolactone copolymers
L-lactide/dl-lactide copolymers
Methyl methacrylate-N-vinyl pyrrolidone copolymers
Modified proteins
Nylon-2
PHBA/$\gamma$-hydroxyvalerate copolymers (PHBA/HVA)
PLA/polyethylene oxide copolymers
PLA-polyethylene oxide (PELA)
Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-$\beta$-hydroxypropionate (PHPA)
Poly-$\beta$-hydroxybutyrate (PBA)
Poly-$\sigma$-valerolactone
Poly-$\beta$-alkanoic acids
Poly-$\beta$-malic acid (PMLA)
Poly-$\epsilon$-caprolactone (PCL)
Pseudo-Poly(Amino Acids)
Starch
Trimethylene carbonate (TMC)
Tyrosine based polymers In practice of the present invention, it is also possible to provide polymer material in the form of granulated or powdered polymers that have been created through a freeze-drying process, or other technique known in the art to create a large amount of intercommunicating surface area to facilitate hydration and pressurized solvation.

In an embodiment of the present invention, there may be benefit to providing an entrapped polymer in particulate or powered form throughout the interconnecting pores of the dried porous material, or alternatively to provide the entrapped polymer powder within a second polymer phase, thereby preventing the powder from packing to close together. The powder should not be allowed to pack together if the reduced porosity interferes with proper hydration across the surface area of the polymer. This embodiment may also be valuable in preventing two or more different powders or particulates from stratifying during storage or shipment.

The high surface area formed by intercommunicating porosity and/or interparticulate space, in conjunction with hydration and pressure are desirable to rapidly solvate the dried porous polymer material into a high concentration gel, paste or putty. Fluid placed in contact with the porous construct should rapidly infiltrate the construct and hydrate the polymer surfaces. Hydration should occur within a short period of time, about 5 minutes, and preferably in less than one minute, in order to expedite the surgical procedure. Once the porous construct is hydrated, pressure is utilized to rapidly solvate the polymer three dimensionally, thus creating a high viscosity gel. This pressure induced solvation process occurs across all hydrated polymer surfaces when exposed to pressure. It is believed that the application of pressure facilitates the permeation of the polymer by the solvating fluids: this infusion allows the polymer molecules to disassociate from one another, thus forming a gel. The pressure induced solvation allows for the creation of polymer solutions at higher concentrations and rates faster than can normally be achieved without pressure (e.g. stagnant solvation) or through other aggressive solubilizing methods (e.g., mechanical shearing, blenders, or other techniques known in the art). As the pressure is increased, the volume of hydration fluid necessary to solvate a given construct is decreased. The volume of fluid utilized to solvate the polymer controls the overall viscosity and concentration of the gel. Furthermore, once solvated into a viscous gel, further addition of solvating fluid, or other fluids and materials, may be utilized to alter the physical characteristics of the gel.

In contrast with the practice of the present invention, a dried porous material, not adequately hydrated, or alternatively, not exposed to sufficient pressure or compression, will form a partially solvated material, wherein regions of solvated gel surround pockets of non-solvated, dry material. This may occur as the polymer material of the dried gel absorbs the fluids, and prevents the solvation of other regions of the material from solvating properly.

The high viscosity gels and putties of the present invention may be utilized in various surgical applications, especially in void filling (e.g. inter-spinal cage, and traumatic bony voids) where there are high levels of irrigation and body fluid turnover. The viscous gels of the present invention may also be used in tissue augmentation, for example in areas such as lips, and pock mark fillings. By providing a dry polymer capable of easily being formed into a putty, the surgeon is provided with the option of utilizing fluids such as saline, blood, platelet rich plasma (PRP) and bone marrow aspirate to hydrate the polymer immediately prior to use. This option is unavailable in currently supplied prehydrated or wet products. Additionally, the application of pressure per the process of the present invention allows for the creation of high concentration solutions from polymers that are too fragile to withstand high shear forces necessary in some aggressive processes. Additionally, particulate, biologically active agents, or other materials may be incorporated that may otherwise be damaged by the aggressive techniques, but are capable of being incorporated through the pressure induced solvation of the present invention. The pressure induced solvation should occur within a short period of time, about 5 minutes, and preferably in less than one minute, in order to expedite the surgical procedure. This allows for the use of biologically active agents having limited lifespans in hydrated form. Additionally, heat or additives (e.g. surfactants, plasticizers, coatings, etc) can be used to modify the time necessary to hydrate and/or solvate the polymer. For example, surfactants are useful in increasing the rate of hydration/solvation of the polymer material, however, this may be undesirable if the polymer is readily soluble. In this instance, a coating or chemical modification of the polymer may be necessary to prevent premature salvation during the hydration process.

The solvating fluid utilized for the practice of the present invention may be aqueous or non-aqueous. The solvating fluid may itself be a liquid polymer or polymer solution. The solvating fluid may be basic, neutral or acidic, as appropriate for solvating the polymer material selected, further, the solvating fluid itself may be a biologically active agent. Non-limiting examples of solvating fluids include saline, whole blood, plasma, Platelet-Rich-Plasma (PRP), Bone-Marrow-Aspirate (BMA), Acetone, Acetic Acid, 1-methyl-2-pyrrolidone (NMP), and dimethyl sulfoxide (DMSO). The polymer and/or resultant polymer gel may be chemically altered (e.g., pH adjusted, exposed to ionizing radiation, etc.) or physically adjusted (e.g., temperature adjusted, whipped, etc.) or otherwise conditioned to modify the physical properties of the polymer gel. In one embodiment, once implanted into a living being, the solvated polymer gel may undergo physical or chemical changes due to interaction with body fluids. Alternatively, these physical or chemical changes may be brought about by interactions of the hydrating fluid and the dry high surface area biomaterial initiated upon hydration or solvation. Additionally, these physical or chemical changes may be initiated by an interaction of two or more hydrating fluids, which are combined just prior to hydration. For example, organic fluids may diffuse out of the polymer gel leaving a semi-solid or solid construct, or the temperature of the body may solidify or liquefy the polymer gel.

In an embodiment of the present invention, the viscous gel may also feature additive materials. The additive materials may be biologically active agents (e.g., drugs, hormones, growth factors, cells, viruses, etc.). Examples of biologically active agents that may be delivered in the device are shown in following Table 2. The additive materials may also include particulate or fibrous filler material (e.g., Ceramics (HA, TCP, etc), Natural Polymers (collagen, Hyaluronan, Alginate, etc), demineralized bone matrix (DBM), metals, synthetic polymers (PLA, PLG, PCL, PMA, etc.)). Other non-limiting examples of suitable filler materials that may be added to the polymer material are listed in Table 3. The additive materials may be soluble or insoluble and may be held within the dry foam prior to saturation, alternatively carried into the foam with the solvating fluid, or added in mechanically (e.g., kneading, blending, etc.) after solvation.

TABLE 2

Examples of Biological Active Ingredients

Adenovirus with or without genetic material
Alcohol
Amino Acids
    L-Arginine
Angiogenic agents
Angiotensin Converting Enzyme Inhibitors (ACE inhibitors)
Angiotensin II antagonists
Anti-angiogenic agents
Antiarrhythmics
Anti-bacterial agents
Antibiotics
    Erythromycin
    Penicillin
Anti-coagulants
    Heparin
Anti-growth factors
Anti-inflammatory agents
    Dexamethasone
    Aspirin
    Hydrocortisone
Antioxidants
Anti-platelet agents TABLE 2-continued Examples of Biological Active Ingredients Forskolin
GP IIb-IIIa inhibitors
    eptifibatide
Anti-proliferation agents
  Rho Kinase Inhibitors
    (+)-trans-4-(1-aminoethyl)-1-(4-pyridylcarbamoyl)
  cyclohexane
Anti-rejection agents
  Rapamycin
Anti-restenosis agents
  Adenosine $A_{2A}$ receptor agonists
Antisense
    Antispasm agents
  Lidocaine
  Nitroglycerin
  Nicarpidine
Anti-thrombogenic agents
  Argatroban
  Fondaparinux
  Hirudin
  GP IIb/IIIa inhibitors
Anti-viral drugs
Arteriogenesis agents
  acidic fibroblast growth factor (aFGF)
  angiogenin
  angiotropin
  basic fibroblast growth factor (bFGF)
  Bone morphogenic proteins (BMP)
  epidermal growth factor (EGF)
  fibrin
  granulocyte-macrophage colony stimulating factor (GM-CSF)
  hepatocyte growth factor (HGF)
  HIF-1
  insulin growth factor-1 (IGF-1)
  interleukin-8 (IL-8)
  MAC-1
  nicotinamide
  platelet-derived endothelial cell growth factor (PD-ECGF)
  platelet-derived growth factor (PDGF)
  transforming growth factors alpha & beta (TGF-.alpha., TGF-beta.)
  tumor necrosis factor alpha (TNF-.alpha.)
  vascular endothelial growth factor (VEGF)
  vascular permeability factor (VPF)
Bacteria
Beta blocker
Blood clotting factor
Bone morphogenic proteins (BMP)
Calcium channel blockers
Carcinogens
Cells
Cellular materials
  Adipose cells
  Blood cells
  Bone marrow
  Cells with altered receptors or binding sites
  Endothelial Cells
  Epithelial cells
  Fibroblasts
  Genetically altered cells
  Glycoproteins
  Growth factors
  Lipids
  Liposomes
  Macrophages
  Mesenchymal stem cells
  Progenitor cells
  Reticulocytes
  Skeletal muscle cells
  Smooth muscle cells
  Stem cells
  Vesicles
Chemotherapeutic agents
  Ceramide
  Taxol
  Cisplatin
Cholesterol reducers
Chondroitin
Collagen Inhibitors Colony stimulating factors
Coumadin
Cytokines prostaglandins
Dentin
Etretinate
Genetic material
Glucosamine
Glycosaminoglycans
GP IIb/IIIa inhibitors
  L-703,081
Granulocyte-macrophage colony stimulating factor (GM-CSF)
Growth factor antagonists or inhibitors
Growth factors
  Bone morphogenic proteins (BMPs)
  Core binding factor A
  Endothelial Cell Growth Factor (ECGF)
  Epidermal growth factor (EGF)
  Fibroblast Growth Factors (FGF)
  Hepatocyte growth factor (HGF)
  Insulin-like Growth Factors (e.g. IGF-I)
  Nerve growth factor (NGF)
  Platelet Derived Growth Factor (PDGF)
  Recombinant NGF (rhNGF)
  Tissue necrosis factor (TNF)
  Transforming growth factors alpha (TGF-alpha)
  Transforming growth factors beta (TGF-beta)
  Vascular Endothelial Growth Factor (VEGF)
  Vascular permeability factor (VPF)
  Acidic fibroblast growth factor (aFGF)
  Basic fibroblast growth factor (bFGF)
  Epidermal growth factor (EGF)
  Hepatocyte growth factor (HGF)
  Insulin growth factor-1 (IGF-1)
  Platelet-derived endothelial cell growth factor (PD-ECGF)
  Tumor necrosis factor alpha (TNF-.alpha.)
Growth hormones
Heparin sulfate proteoglycan
HMC-CoA reductase inhibitors (statins)
Hormones
  Erythropoietin
Immoxidal
Immunosuppressant agents
inflammatory mediator
Insulin
Interleukins
Interlukin-8 (IL-8)
Interlukins
Lipid lowering agents
Lipo-proteins
Low-molecular weight heparin
Lymphocites
Lysine
MAC-1
Methylation inhibitors
Morphogens
Nitric oxide (NO)
Nucleotides
Peptides
Polyphenol
PR39
Proteins
Prostaglandins
Proteoglycans
  Perlecan
Radioactive materials
  Iodine - 125
  Iodine - 131
  Iridium - 192
  Palladium 103
Radio-pharmaceuticals
Secondary Messengers
  Ceramide
Somatomedins
Statins
Stem Cells
Steroids
Thrombin
Thrombin inhibitor

TABLE 2-continued

Examples of Biological Active Ingredients

Thrombolytics
Ticlid
Tyrosine kinase Inhibitors
    ST638
    AG-17
Vasodilators
    Histamine
    Forskolin
    Nitroglycerin
Vitamins
    E
    C
Yeast
Ziyphi fructus

TABLE 3

Examples of suitable filler materials

Alginate
Bioglass
Calcium
Calcium Phosphates
Ceramics
Chitin
Chitosan
Cyanoacrylate
Collagen
Dacron
Demineralized bone
Elastin
Fibrin
Gelatin
Glass
Gold
Hyaluronic acid
Hydrogels
Hydroxy apatite
Hydroxyethyl methacrylate
Hyaluronic Acid
Liposomes
Mesenchymal cells
Nitinol
Osteoblasts
Oxidized regenerated cellulose
Phosphate glasses
Polyethylene glycol
Polyester
Polysaccharides
Polyvinyl alcohol
Platelets, blood cells
Radiopacifiers
Salts
Silicone
Silk
Steel (e.g. Stainless Steel)
Synthetic polymers
Thrombin
Titanium The inclusion of groups and subgroups in the tables is exemplary and for convenience only. The grouping does not indicate a preferred use or limitation on use of any material therein. For example, in Table 2, the groupings are for reference only and not meant to be limiting in any way (e.g., it is recognized that the Taxol formulations are used for chemotherapeutic applications as well as for anti-restenotic coatings). Additionally, the table is not exhaustive, as many other drugs and drug groups are contemplated for use in the current embodiments. There are naturally occurring and synthesized forms of many therapies, both existing and under development, and the table is meant to include both forms.

The dry porous foam of the present invention provides the benefit of dry sterilization that reduces the amount of damage done by high energy sources of sterilization (e.g., gamma, e-beam, etc.) or allows the use of gas sterilization (e.g., plasma, ETO, etc.) that are unavailable to wet gel formulations. Additionally the dry foam may serve to orient the biologically active agents and/or filler materials, and may serve to prevent stratification of the materials during storage and shipment. The viscous gel, created as the foam collapses, facilitates migration of the entrapped additive materials, such as biologically active agents and/or filler materials, through the tip of a syringe by preventing aggregations at the narrowing, and ensuring even flow of the gel through a narrow opening. Additionally, the present invention allows for the use of unique syringe packaging systems that allow saturation of the foam in ways that reduces the formation of gas bubbles within the gel.

In the practice of one embodiment of the present invention, the physician places the sterilized, dry porous foam into a suitable container (e.g., tray, bowl, etc.) and saturates the foam with a desired amount of fluid. Preferably, less fluid is used to saturate the foam than was originally present in manufacturing the porous foam, in order to create a gel of higher concentration. The porous foam and hydrating fluid may then be kneaded and compressed to solubilize the porous polymer foam into a malleable gel, paste or putty. In a preferred embodiment of the present invention, the packaging housing the foam may be in the form of a syringe adapted to provide an avenue of egress for air or gases occupying the porosity of the foam as pressure is applied. In this way, the hydrating fluid can be injected into the foam porosity and pressurized to facilitate solubilization and collapse of the porous material into the gel, paste or putty without requiring kneading. Instead, the fluid is forced into the polymer mass by compressing the mixture with the plunger of the syringe. If desired, resultant material can then be directly injected into a body.

For clarity, the term "gel" in this disclosure is defined as a solution or suspension having increased viscosity when compared to the original hydrating fluid. Examples of synonyms utilized in this disclosure include "paste" and "putty".

The term "hydration", and its derivatives, are used to define the absorption of fluid into the porosity of the polymer foam or around particles of polymer.

The term "solublize", and its derivatives, are used to define the collapse of the polymer into a solution, colloidal suspension or combination of the two.

The terms "pressure" and "compression" may be used interchangeably as the force needed to induce collapse and solubilization of the polymer.

The term "biodegradable" is meant to include those definitions used for "bioabsorbable" and "bioresorbable".

The above-described porous device suitable for pressurized solubilization to form a highly viscous flowable to non-flowable gel material has many commercial uses, including, but not limited to, tissue repair, tissue void filling and tissue augmentation. In particular, the device is useful as a bone void filler. This bone void filler device may preferably contain additive materials. Additive materials may include fillers, or materials to aid in bone healing (e.g., demineralized bone matrix (DBM), calcium phosphate and its derivatives, such as hydroxyapatite or beta-Tricalcium Phosphate, insoluble collagen, etc.) The porous device capable of pressurized solubilization may also be used as a delivery depot for biologically active agents with characteristics of immediate release and/or sustained release. This delivery depot embodiment may be used to deliver biologically active agents (e.g., drugs, vaccines, antibiotics, cancer drugs, anti-adhesion drugs, biologics including hormones, growth factors, angiogenic or anti-angiogenic factors, proteins, or polysaccharides). Another application may include use as an injectable material for anti-adhesion, and treatment of osteoarthritis.

Hence, in one aspect, the invention resides in a method of producing a viscous gel from a dry high porosity structure, featuring the steps of:
  a) Contacting a polymer, capable of dissolving in fluids, with a fluid, to form a solution, colloidal suspension or slurry;
  b) Casting the solution, suspension or slurry into a tray or mold;
  c) Removing the fluid to leave a dry high porosity, high surface area structure;
  d) Packaging and sterilizing the dry high porosity, high surface area structure; and
  e) Rehydrating and pressure induced solvating the dry high porosity structure.

In another aspect, the invention resides in a method of producing a dry high porosity, high surface area structure capable of becoming a viscous gel, featuring the steps of:
  a) Combining a polymer, capable of dissolving in fluids, with a fluid, to form a solution, colloidal suspension or slurry;
  b) Chemically or physically conditioning said solution, suspension or slurry;
  c) Casting the conditioned solution or slurry into a tray or mold;
  d) Removing said fluid to leave a dry, high surface area, low density porous structure;
  e) Packaging and sterilizing the dry, high surface area, low density porous structure; and
  f) Rehydrating and pressure induced solvating the dry, high surface area, porous structure.

In another aspect, the invention resides in a method of producing a dry high porosity, high surface area structure with additive capable of becoming a viscous gel, featuring the steps of:
  a) Combining a polymer, capable of dissolving in fluids, with a fluid, to form a solution, colloidal suspension or slurry;
  b) Admixing a additive into the suspension or slurry;
  c) Casting the solution or slurry with additive into a tray or mold;
  d) Removing the fluid to leave a dry high porosity structure containing an additive;
  e) Packaging and sterilizing the dry, high surface area, compounded porous structure; and
  f) Rehydrating and pressure induced solvating the dry, high surface area, compounded, porous structure.

In another aspect, the invention resides in a method of producing a dry porous, low density, high surface area structure capable of becoming a viscous gel, featuring the steps of:
  a) Combining a first polymer in particulate form, capable of dissolving in aqueous fluids, with a non-aqueous solvent that will not solvate the first polymer wherein the solvent contains a second dissolved polymer;
  b) Casting the second polymer solvent mixture containing the first polymer particulate into a tray or mold;
  c) Removing the solvent to leave a dry low density, high surface area, porous second polymer structure supporting the first polymer particulate;
  d) Packaging a sterilizing the dry low density, high surface area, porous second polymer structure containing the first polymer particulate; and
  e) Rehydrating and pressure induced solvating the dry high porosity, high surface area structure.

In a preferred embodiment, the bioresorbable polymer is prepared as a low viscosity solution, which is then lyophilized into a high porosity, high surface area, low density foam that may be placed into a syringe, and optionally sterilized, to await hydration and solubilization. The polymer within the syringe can be hydrated and solubilized under pressure with a volume of biocompatible fluid (e.g. saline, blood, etc) that is less than the volume of fluid removed during lyophilization, thereby creating a viscous gel.

Such gel is useful as an injectable or implantable augmentation material, suitable for uses such as lip and nipple enhancement, wrinkle line filling, or as tissue void filler for such areas as biopsy sites. If desired, additive materials, such as biologically active agents (e.g. antibiotic, growth factor, etc.) may be incorporated into the lyophilized foam or hydration/solvation fluid. Additionally, fragile biologically active agents (e.g. drugs, cells, cellular components, etc.) can be selectively placed into the hydration/solvation fluid thus avoiding possible damage caused by lyophilization, sterilization or storage. In order to create a longer lasting or permanent affect, a slow degrading particulate (e.g. insoluble natural polymer fibers, biodegradable synthetic polymer microspheres, ceramics, etc.) or nondegradable particulate (e.g. PMMA, microspheres, bioglass beads, etc.) can be incorporated into the lyophilized polymer.

In another embodiment, the bioresorbable high porosity foam is hydrated and solubilized under pressure to create a delivery depot for biologically active agents useful in the treatment of cancer, or as extended delivery systems for biologically active agents such as hormones, and vaccines. These biologically active agents can be lyophilized into the porous polymer, impregnated into slow release particulates that are suspended in the porous polymer, suspended in the hydration/solvation fluid, or mechanically added after pressure induced solvation.

In another embodiment, a non-soluble particulate or fiber that may or may not be bioresorbable is incorporated into the lyophilized polymer foam to improve mechanical properties of the gel formed during pressurized solubilization. This non-soluble particulate improves resistance to washout when the gel is used as a tissue void filler and can further function as scaffolding for cellular attachment. Such gels are specifically useful for bone void filling, and may further incorporate and deliver growth factors (e.g., BMP, etc.)

In order to solubilize the gel with a minimal amount of trapped gas within the gel, combination hydration/compressive-solvation systems are used to fill the porosity with fluid while allowing the gas to escape during the hydration or compression induced solubilization step. The hydration/compressive-solvation systems and the uses of the present invention are depicted in the attached non-limiting figures. It should be noted that for filler applications involving post-placement imaging, that gas bubbles may be desirable to increase the contrast between tissue and filler material. Thus it may be desirable to hydrate, and compressively solvate the unit without allowing complete escape of gas.

FIG. 1 depicts the cross-section of a syringe hydration system 100 having a delivery needle 110 with vent ports 120. On either end there is a receiving syringe connection 130 and a delivery syringe connection 140. FIG. 2 shows completed assembly 200 of delivery syringe 210, hydration system 220 and receiving syringe 230. As plunger 240 of the delivery syringe 210 is depressed fluid 250 is injected into the bottom of receiving syringe 230. The air displaced by the injected fluid 260 is forced out of vent ports 270. Once porous polymer 280 is hydrated, the syringe hydration system is removed and the hydrated material contained in the receiving syringe is pressurized by forcing plunger 290 in while preventing egress by occluding the tip of receiving syringe 230.

Another assembly shown in FIG. 3 depicts a hydration/compressive solvation assembly 300 composed of delivery syringe 310 and receiving syringe 320 joined by fluid exchange connector 330. Thus assembled, the fluid 333 contained in the delivery syringe can be injected into the porous polymer 340 contained in the receiving syringe. As the air or gas in the porosity of the polymer is displaced by the injected fluid 333, it escapes through micro-vent holes 350 in the plunger 360 of the receiving syringe 320. The fluid 333 occludes the micro-vent holes 350 on contact allowing the now hydrated product to be compressed by forcing plunger 360 into the syringe 320 while preventing movement of plunger 370 of the delivery syringe 310.

FIG. 4 depicts hydration/compressive solvation assembly 400 wherein the delivery syringe 410 injects fluid 420 into the back of receiving syringe 430. As the fluid displaces air or gas from porous polymer 440 it escapes through porous pressure cap 450. Once hydrated, pressure is applied by using delivery syringe 410 as the plunger for receiving syringe 430 and compressing the hydrated polymer matrix against porous pressure cap 450. As the pressure is increased, the polymer solubilizes in the fluid. Removal of the pressure cap and expressing of the solvated polymer is shown in FIG. 5.

FIG. 5 depicts hydration/compressive solvation assembly 500 expressing solvated polymer matrix 510 from receiving syringe 520. Delivery syringe 530, having injected its fluid cargo, now functions as the plunger for receiving syringe 520.

FIG. 6 depicts hydration/compressive solvation assembly 600 supporting fluid injection port 610. Once fluid has been injected into the assembly, valve 620 is closed. Plunger 630 is then used to force the injected fluid into porous polymer 640, displacing any air or gas from the polymer that escapes through porous pressure cap 650. Once fluid reaches the cap, it becomes occluded and the pressure inside of the syringe increases resulting in uniform three-dimensional solvation of the porous polymer foam creating a gel.

FIG. 7 depicts combination delivery-receiving syringe assembly 700. This assembly receives fluid through filling port 710. Plunger 720 is then depressed to deliver and confine fluid 730 within main barrel 740 of the assembly. Once plunger 720 is fully seated, plunger 750 is depressed to completely hydrate porous polymer 760 and expel any air or gas. A pressure cap (not shown) is then place over the tip of the assembly to allow pressure to build as plunger 750 is further depressed. The pressure induces uniform solvation of porous polymer 760.

Figure 8:
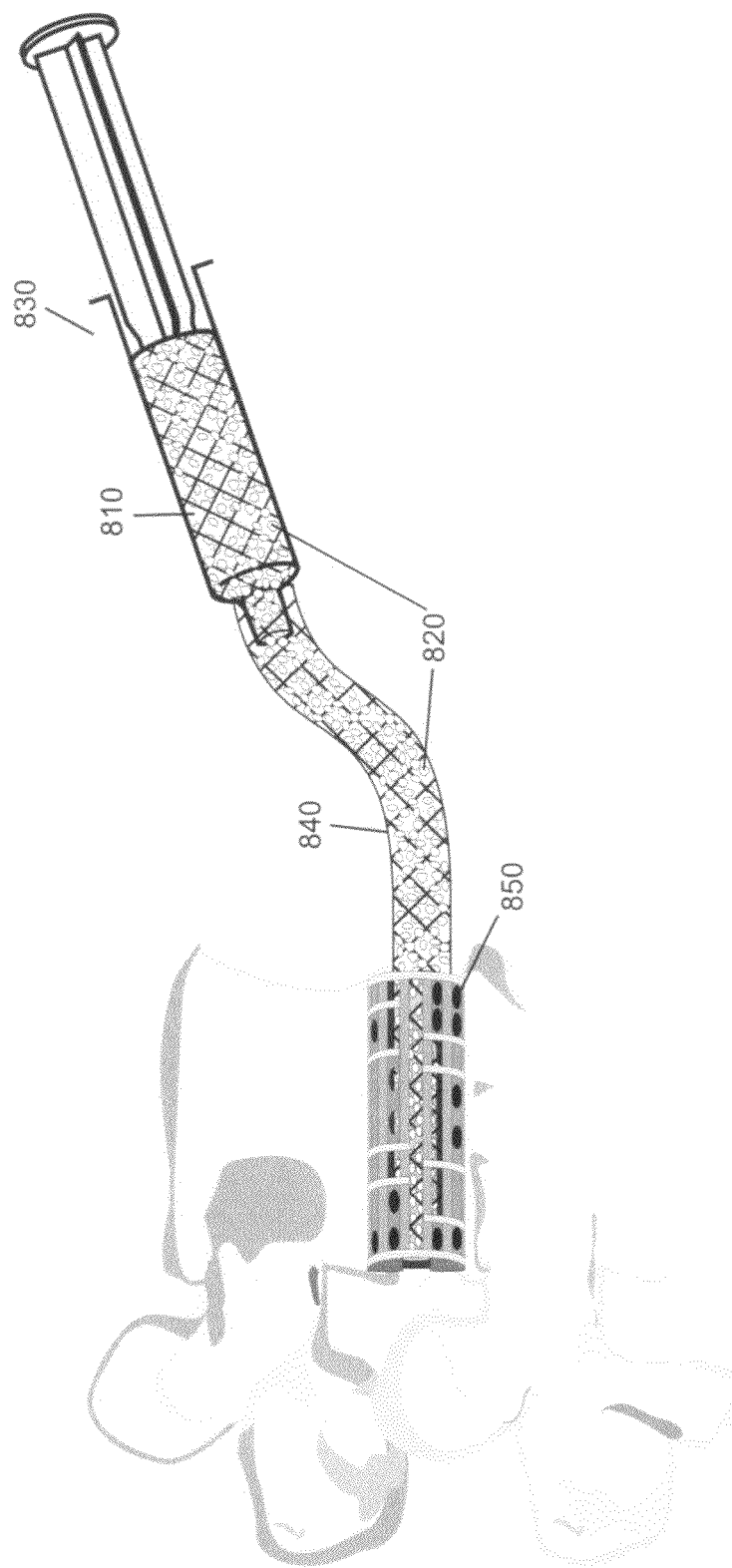
FIG. 8 depicts delivery of a ceramic carrying gel injected through a cannula into a spinal cage.

FIG. 8 depicts pressure solvated polymer gel 810 with suspended ceramic particulate 820 being delivered by syringe 830 through cannula 840 into spinal fusion cage 850.

Figure 9A:
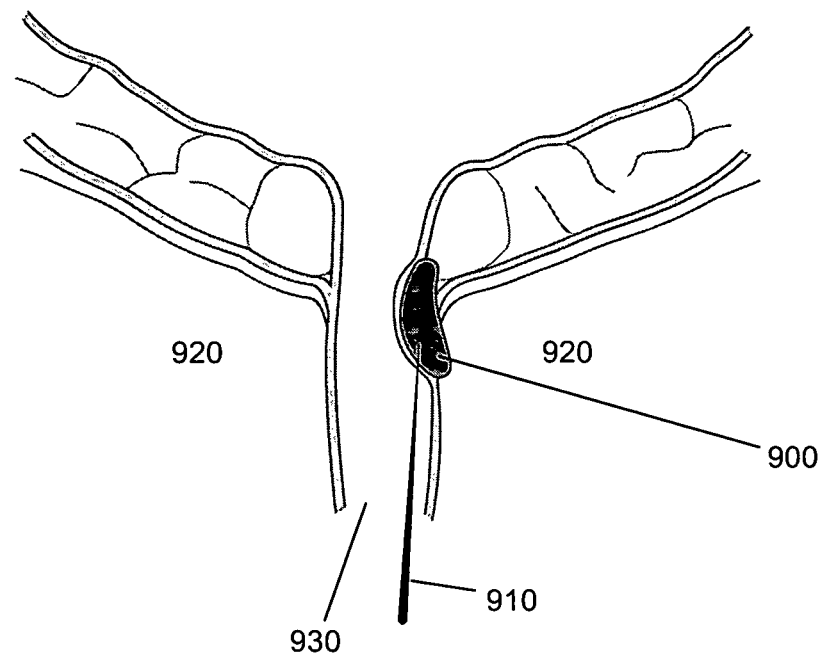
FIG. 9 depicts delivery of a gel as a periurethrial bulking agent.
Figure 9B:
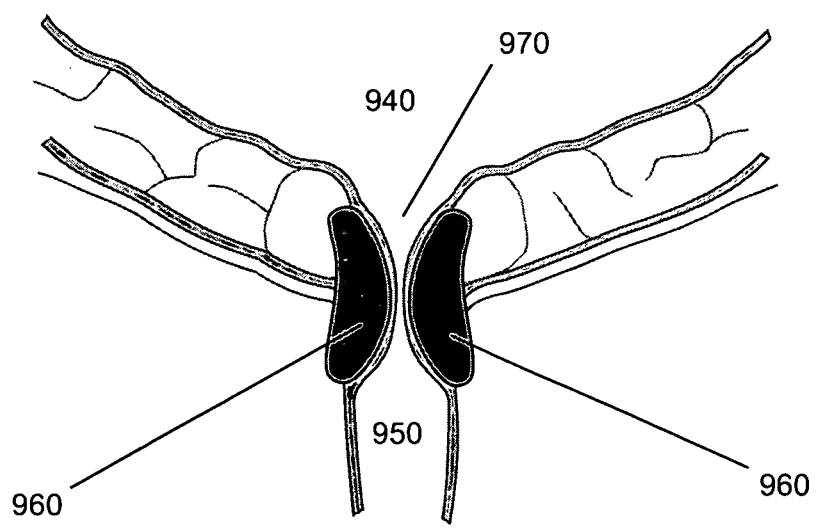

FIG. 9 depicts soft tissue injection and augmentation that is adding bulk around the neck of the urinary bladder to reduce or eliminate urinary stress incontinence. FIG. 9A shows delivery of compression solvated polymer gel 900 via injection needle 910 into tissues 920 surrounding urethra 930. FIG. 9B shows bladder 940 separated from the lumen of urethra 950 by narrowing 960. This narrowing is caused by the presence of injected compression solvated polymer 970.

The following examples are set forth to illustrate the various uses and embodiments of the present invention. These examples are provided for the purpose of illustration only and are not intended to be limiting in any sense.

A polymer matrix material useful for the present invention can be manufactured by the following method:

500 grams of a 1% by weight acid soluble collagen solution (Semed S, supplied by Kensey Nash Corporation) is poured onto a tray at a thickness of 4 mm and frozen on a block of dry ice. After freezing, the sheet is lyophilized using a Savant SuperModulo Freeze-Dryer for 24 hours at 200 millitorr. The resultant 5 gram porous sheet is cut into 50 equal parts and stored in a freezer within a sealed nitrogen gas filled bag.

Example 1

A single 0.1-gram porous collagen sheet of matrix material is placed in a shallow dish and covered with 1.9 grams of buffered saline at a pH of 7.4 that is allowed to soak in and spread across the internal surfaces of the pores by capillary rehydration. After 1 minute the sheet is kneaded and compressed by hand while folding any dry areas into the moist center of the mass to create approximately 2 cc of 5% putty. A putty made in this manner has a viscoelastic property similar to soft tissue, and thus makes an ideal augmentation material.

Example 2

The 5% putty from Example 1 was placed into a small container and covered with 40 cc of buffered saline at a pH of 7.4. After 4 hours the material is still intact with no sign of softening, swelling or taking on moisture. The putty is then kneaded and compressed while in contact with 1 gram of buffered saline at a pH of 7.4 to create approximately 3 cc of 3.3% putty. A putty made in this manner is easily injected through long needles and thus makes an ideal deep injection augmentation material.

Example 3

A single 0.1-gram porous collagen sheet of matrix material is rolled and placed into a 10 cc syringe. Using a 14 g I.V. needle, 1.9 grams of buffered saline at a pH of 7.4 is injected from a separated delivery syringe into the bottom of the syringe containing the rolled collagen sheet. After removing the needle, the plunger to the syringe containing the rolled collagen and saline is depressed, crushing the porosity of the hydrated region of the sponge and forcing the fluid into the non-hydrated portions of the sponge. Once fully hydrated, a syringe cap is placed over the opening and the plunger compressed to pressurize the interior of the syringe and solvate the polymer. The cap is removed and smooth, homogeneous 5% putty is expelled from the syringe. This material has physical properties identical to example 1.

Example 4

A single 0.1-gram porous collagen sheet of matrix material is rolled and placed into a 10 cc syringe. The plunger of the syringe is depressed to the 2 cc mark, crushing the collagen sponge, which reduces the porosity without changing the surface area of the pore walls. Using a 14 g I.V. needle, 1.9 grams of buffered saline at a pH of 7.4 is injected from a separated delivery syringe into the bottom of the syringe containing the crushed collagen roll. After removing the needle, a syringe cap is placed over the opening and the syringe was allowed to rest so that the sponge could completely hydrate. After 2 minute the plunger is compressed to pressurize the interior of the syringe and solvate the collagen. The cap is removed and smooth, homogeneous 5% putty is expelled from the syringe. This material has physical properties identical to examples 1 and 3.

Example 5

A single 0.1-gram porous collagen sheet of matrix material is rolled and placed into a 10 cc syringe. Using a 14 g I.V. needle, 2 grams of porcine blood is injected from a separate delivery syringe into the bottom of the syringe containing the rolled collagen sheet. After removing the needle, the plunger to the syringe containing the rolled collagen and blood is depressed, crushing the porosity of the hydrated region of the sponge and forcing the blood into the non-hydrated portions of the sponge. Once fully hydrated, a syringe cap is placed over the opening and the plunger compressed to pressurize the interior of the syringe and solvate the polymer. The cap is removed and thick, homogeneous 5% putty is expelled from the syringe.

Matrix material, containing a particulate, useful for the present invention can be manufactured by the following method:

500 grams of a 5% by weight acid soluble collagen solution (Semed S, supplied by Kensey Nash Corporation) combined with 75 grams of 500 micron particle size hydroxylapatite, is poured onto a tray at a thickness of 4 mm and frozen on a block of dry ice. After freezing, the sheet is lyophilized using a Savant SuperModulo Freeze-Dryer for 24 hours at 200 millitorr. The resultant 100-gram porous ceramic/collagen sheet is cut into 50 equal parts and stored in a freezer within a sealed nitrogen gas filled bag.

Example 6

A single 2-gram porous sheet of particulate containing matrix material is placed in a shallow dish and covered with 4.5 grams of buffered saline at a pH of 7.4 that is allowed to soak in and spread across the internal surfaces of the pores. The hydrophilic nature of the hydroxylapatite improves the rate of hydration. After 1 minute the sheet is kneaded and compressed by hand while folding any dry areas into the moist center of the mass to create approximately 5 cc of 75/25 ceramic to collagen putty wherein the collagen is solubilized to approximately 10% by weight of saline. A putty made in this manner has properties suitable for use as a bone void filler.

Matrix material, containing two different particulates, useful for the present invention can be manufactured by the following method:

500 grams of a 5% by weight acid soluble collagen solution (Semed S, supplied by Kensey Nash Corporation) combined with 15 grams of insoluble fibrous collagen (Semed F, supplied by Kensey Nash Corporation) and 120 grams of 500 micron particle size hydroxylapatite, is poured onto a tray at a thickness of 4 mm and frozen on a block of dry ice. After freezing, the sheet is lyophilized using a Savant SuperModulo Freeze-Dryer for 24 hours at 200 millitorr. The resultant 100-gram porous ceramic/collagen sheet is cut into 50 equal parts and stored in a freezer within a sealed nitrogen gas filled bag.

Example 7

A single 3.2-gram porous matrix material containing two different particulates is placed in a 10 cc syringe having a 3.6 mm diameter opening. Using a 14 g I.V. needle, 4.5 grams of buffered saline at a pH of 7.4 is injected from a separate delivery syringe into the bottom of the syringe containing the porous sheet material. After removing the needle, the plunger to the syringe containing the collagen/ceramic and saline is depressed, crushing the porosity of the hydrated region of the sponge and forcing the fluid into the non-hydrated portions of the sponge. Once fully hydrated, a syringe cap is placed over the syringe opening and the plunger compressed to pressurize the interior of the syringe and solvate the acid soluble collagen. The cap is removed and homogeneous 75/9/16 ceramic/fibrous-collagen/soluble-collagen putty is expelled from the syringe wherein the soluble collagen forms approximately a 10% solution by weight of saline. This material has properties similar to those in example 6, but with higher resistance to washout due to the fibrous content.

A synthetic polymer matrix material containing particulate useful for the present invention can be manufactured by the following method:

500 grams of a 5% (by mass) d,d-l,l-polylactic acid (Purac)/dioxane solution combined with 75 grams of 500 micron particle size hydroxylapatite, is spread onto a tray at a thickness of 5 mm and frozen on a block of dry ice. After freezing, the sheet is lyophilized using a Savant SuperModulo Freeze-Dryer for 72 hours at 200 millitorr. The resultant 100-gram porous ceramic/polymer sheet is cut into 50 equal parts and stored in a freezer within a sealed nitrogen gas filled bag.

Example 8

A single 2-gram porous synthetic polymer sheet material containing particulate is placed in a 10 cc syringe having a 3.6 mm diameter opening. Using a 14 g I.V. needle, 4.5 grams of acetone is injected from a separate delivery syringe into the bottom of the syringe containing the porous sheet material. After removing the needle, the plunger to the syringe containing the ceramic/polymer foam and acetone is depressed, crushing the porosity of the hydrated region of the sponge and forcing the fluid into the non-hydrated portions of the sponge. Once fully hydrated, a syringe cap is placed over the syringe opening and the plunger compressed to pressurize the interior of the syringe and solvate the polymer. The cap is removed and homogeneous 75/25-ceramic/-polymer putty is expelled from the syringe into 50 cc of phosphate buffered saline wherein the polymer forms approximately a 10% solution by weight of acetone. The putty instantly forms a tough outer skin as acetone is leached from the polymer. After 4 hours the ceramic/polymer mass appears to be completely solidified and can be fractured to disclose an internal porosity. This putty has properties suitable for use as a settable bone void filler.

Example 9

A dry blend containing 8 cc of 500 micron particle size hydroxylapatite and 2 cc of dry hyaluronic acid powder (LifeCore Medical, Chaska Minn.) is spread evenly on the bottom of a glass dish and saturated with 10 cc of a 0.5% d,d-l,l-polylactic acid solution in dioxane. The composite is frozen on a block of dry ice and then lyophilized using a Savant SuperModulo Freeze-Dryer for 48 hours at 200 millitorr. The resultant porous sheet is composed of two separate particulate phases held in a fixed special relationship to each other by a fragile interpenetrating porous PLA phase. This dry three-phase material is suitable as a bone paste when hydrated and pressure solubilized. In order to accomplish this the three-phase sheet is placed in a shallow dish and covered with 5 cc of buffered saline at a pH of 7.4 that is allowed to soak in and spread across the internal surfaces of the porous PLA while engulfing the individual particulates held there. After 1 minute the sheet is kneaded and compressed by hand while folding any dry areas into the moist center of the mass to create approximately 5 cc of a three-phase putty. The compressive kneading rips apart the fragile PLA sheet, reducing it to fibers, particles or granules while in turn solvating the hyaluronic acid. The solvated hyaluronic acid suspends both the hydroxylapatite particles and PLA fibers, particles or granules. This putty has properties suitable for use as a bone void filler and provides stable, insoluble platforms for cellular attachment.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. A process for manufacturing an implantable gel material comprising the steps of:
   a. providing a solution comprising a polymeric biomaterial dissolved in a first volume of a first fluid;
   b. lyophilizing said first fluid, thereby forming a lyophilized polymeric biomaterial having a large surface area;
   c. combining said lyophilized polymeric biomaterial and a rehydrating fluid, wherein said surface area of said lyophilized polymeric biomaterial becomes coated with said rehydrating fluid, and further wherein a second volume of said rehydrating fluid is less than said first volume of said first fluid removed by lyophilization; and
   d. solvating said polymeric biomaterial by applying a pressurizing force and no mechanical shearing to said combined rehydrating fluid and lyophilized polymeric biomaterial, whereby said polymeric biomaterial collapses into a gel exhibiting a viscoelastic property.

2. The process of claim 1, wherein said rehydrating fluid further comprises at least one biologically active agent.

3. The process of claim 1, wherein said biomaterial further comprises at least one biologically active agent.

4. The process of claim 1, wherein said biomaterial further comprises at least one filler material.

5. The process of claim 1, wherein said rehydrating thud further comprises at least one filler material.

6. The process of claim 1, wherein both fluids comprise water.

7. The process of claim 1, wherein at least one fluid comprises saline.

8. The process of claim 1, wherein said polymeric biomaterial is selected from the group consisting of soluble collagen and PLA.

9. The process of claim 4, wherein said filler material comprises at least one member selected from the group consisting of hydroxylapatite and fibrous collagen.

10. The process of claim 1, wherein said implantable gel material further comprises at least one biologically active agent.

11. A process for manufacturing an implantable gel material comprising the steps of:
    a. providing a solution comprising a polymeric biomaterial dissolved in a first fluid;
    b. lyophilizing said first fluid to form a lyophilized polymeric biomaterial;
    c. combining said lyophilized polymeric biomaterial and a rehydrating fluid, wherein said surface area of said lyophilized polymeric biomaterial becomes coated with said rehydrating fluid; and
    d. solvating said polymeric biomaterial by applying a pressurizing force and no mechanical shearing to said combined rehydrating fluid and polymeric biomaterial, whereby said polymeric biomaterial collapses into a viscous gel.

12. The process of claim 11, wherein a volume of said rehydrating fluid is less than a volume of said first fluid removed during lyophilization.

13. The process of claim 11, wherein said pressurizing force consists essentially of a compressive force.

* * * * *